United States Patent
Li et al.

(10) Patent No.: US 8,712,525 B2
(45) Date of Patent: Apr. 29, 2014

(54) METHOD AND APPARATUS FOR CLOSED-LOOP CONTROL OF ANTI-TACHYARRHYTHMIA PACING USING HEMODYNAMIC SENSOR

(75) Inventors: Dan Li, Shoreview, MN (US); Cheng Zhang, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 903 days.

(21) Appl. No.: 12/877,583

(22) Filed: Sep. 8, 2010

(65) Prior Publication Data

US 2010/0331905 A1 Dec. 30, 2010

Related U.S. Application Data

(62) Division of application No. 11/422,101, filed on Jun. 5, 2006, now Pat. No. 7,801,608.

(51) Int. Cl.
*A61N 1/362* (2006.01)

(52) U.S. Cl.
USPC ............................ 607/28; 607/14; 600/526

(58) Field of Classification Search
None
See application file for complete search history.

(56) References Cited

U.S. PATENT DOCUMENTS

| | | | |
|---|---|---|---|
| 4,114,628 A | 9/1978 | Rizk | |
| 5,105,810 A | 4/1992 | Collins et al. | |
| 5,161,527 A | 11/1992 | Nappholz et al. | |
| 5,163,429 A | 11/1992 | Cohen | |
| 5,702,427 A | 12/1997 | Ecker et al. | |
| 5,999,854 A | 12/1999 | Deno et al. | |
| 6,038,476 A | 3/2000 | Schwartz | |
| 6,167,308 A | 12/2000 | DeGroot | |
| 6,775,572 B2 | 8/2004 | Zhu et al. | |
| 2003/0083702 A1* | 5/2003 | Stadler et al. | 607/14 |
| 2005/0070966 A1 | 3/2005 | Sharma | |
| 2005/0070967 A1 | 3/2005 | Zhu et al. | |
| 2005/0075676 A1 | 4/2005 | Deno et al. | |
| 2007/0088221 A1 | 4/2007 | Stahmann | |
| 2007/0282381 A1 | 12/2007 | Li | |

OTHER PUBLICATIONS

"U.S. Appl. No. 11/422,101, Non-Final Office Action mailed Oct. 14, 2009", 12 Pgs.
"U.S. Appl. No. 11/422,101, Notice of Allowance mailed May 17, 2010", 6 pgs.
"U.S. Appl. No. 11/422,101, Response filed Feb. 16, 2010 to Non Final Office Action mailed Oct. 14, 2009", 12 pgs.
"U.S. Appl. No. 11/422,101, Response filed Jul. 14, 2009 to Restriction Requirement mailed Jun. 15, 2009", 9 pgs.
"U.S. Appl. No. 11/422,101, Restriction Requirement mailed Jun. 15, 2009", 9 pgs.
Reynolds, D W, et al., "Measurement of pulmonary artery diastolic pressure from the right ventricle", J Am Coll Cardiol., 25(5), (Apr. 1995), 1176-82.

* cited by examiner

*Primary Examiner* — Kennedy Schaetzle
(74) *Attorney, Agent, or Firm* — Schwegman Lundberg & Woessner, P.A.

(57) ABSTRACT

A cardiac rhythm management (CRM) system includes an implantable medical device that delivers anti-tachyarrhythmia therapies including anti-tachyarrhythmia pacing (ATP) and a hemodynamic sensor that senses a hemodynamic signal. The implantable medical device includes a hemodynamic sensor-controlled closed-loop ATP system that uses the hemodynamic signal for ATP capture verification. When ATP pulses are delivered according to a selected ATP protocol to terminate a tachyarrhythmia episode, the implantable medical device performs the ATP capture verification by detecting an effective cardiac contraction from the hemodynamic signal. The ATP protocol is adjusted using an outcome of the ATP capture verification.

20 Claims, 8 Drawing Sheets

METHOD AND APPARATUS FOR CLOSED-LOOP CONTROL OF ANTI-TACHYARRHYTHMIA PACING USING HEMODYNAMIC SENSOR

CLAIM OF PRIORITY

This application is a divisional of and claims the benefit of priority under 35 U.S.C. §120 to U.S. patent application Ser. No. 11/422,101, filed on Jun. 5, 2006, now U.S. Pat. No. 7,801,608, which is hereby incorporated by reference herein in its entirety.

TECHNICAL FIELD

This document relates generally to cardiac rhythm management (CRM) systems and particularly to a hemodynamic sensor-controlled closed-loop anti-tachyarrhythmia pacing (ATP) system.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrioventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filed with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers an electric shock to terminate a detected tachyarrhythmia episode by depolarizing the entire myocardium simultaneously and rendering it refractory.

Another type of electrical therapy for tachyarrhythmia is anti-tachyarrhythmia pacing (ATP). In ATP, the heart is competitively paced in an effort to interrupt the reentrant loop causing the tachyarrhythmia. An exemplary ICD includes ATP and defibrillation capabilities so that ATP is delivered to the heart when a non-fibrillation VT is detected, while a defibrillation shock is delivered when fibrillation occurs. Although cardioversion and/or defibrillation are effective in terminating tachyarrhythmia, it consumes a large amount of power and results in patient discomfort owing to the high voltage of the shock pulses. It is desirable, therefore, for the ICD to use ATP to terminate a tachyarrhythmia whenever possible.

The efficacy of ATP in terminating tachyarrhythmia depends on the type of the tachyarrhythmia and the timing of ATP delivery. To be effective, an ATP therapy is to be delivered to the heart during an excitable gap in the reentrant loop. Inaccurate timing of an ATP delivery is known to contribute to the failure in terminating tachyarrhythmia using ATP. Therefore, in addition to determining whether ATP is suitable for treating a detected tachyarrhythmia, there is a need to control and optimize the timing of ATP delivery.

SUMMARY

A CRM system includes an implantable medical device that delivers anti-tachyarrhythmia therapies including ATP and a hemodynamic sensor that senses a hemodynamic signal. The implantable medical device includes a hemodynamic sensor-controlled closed-loop ATP system that uses the hemodynamic signal for ATP capture verification. When ATP pulses are delivered according to a selected ATP protocol to terminate a tachyarrhythmia episode, the implantable medical device performs the ATP capture verification by detecting an effective cardiac contraction from the hemodynamic signal. The ATP protocol is adjusted using an outcome of the ATP capture verification.

In one embodiment, a CRM system includes an implantable hemodynamic sensor and an implantable medical device. The implantable hemodynamic sensor senses a hemodynamic signal. The implantable medical device includes a pacing circuit that delivers pacing pulses, including ATP pulses, and an ATP controller. The ATP controller includes an ATP delivery controller and an ATP capture verification module. The ATP delivery controller controls the delivery of the ATP pulses according to an ATP protocol. The ATP capture verification module performs an ATP capture verification during the delivery of the ATP pulses by detecting an effective cardiac contraction using the hemodynamic signal. The effective cardiac contraction is indicated by a detectable event in the hemodynamic signal.

In one embodiment, a method for ATP is provided. A hemodynamic signal is sensed. A predetermined type tachyarrhythmia episode is detected. In response to the detection of the predetermined type tachyarrhythmia episode, ATP pulses are delivered according to an ATP protocol. An ATP capture verification is performed during the delivery of the ATP pulses by detecting an effective cardiac contraction using the hemodynamic signal. The effective cardiac contraction is indicated by a detectable event in the hemodynamic signal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
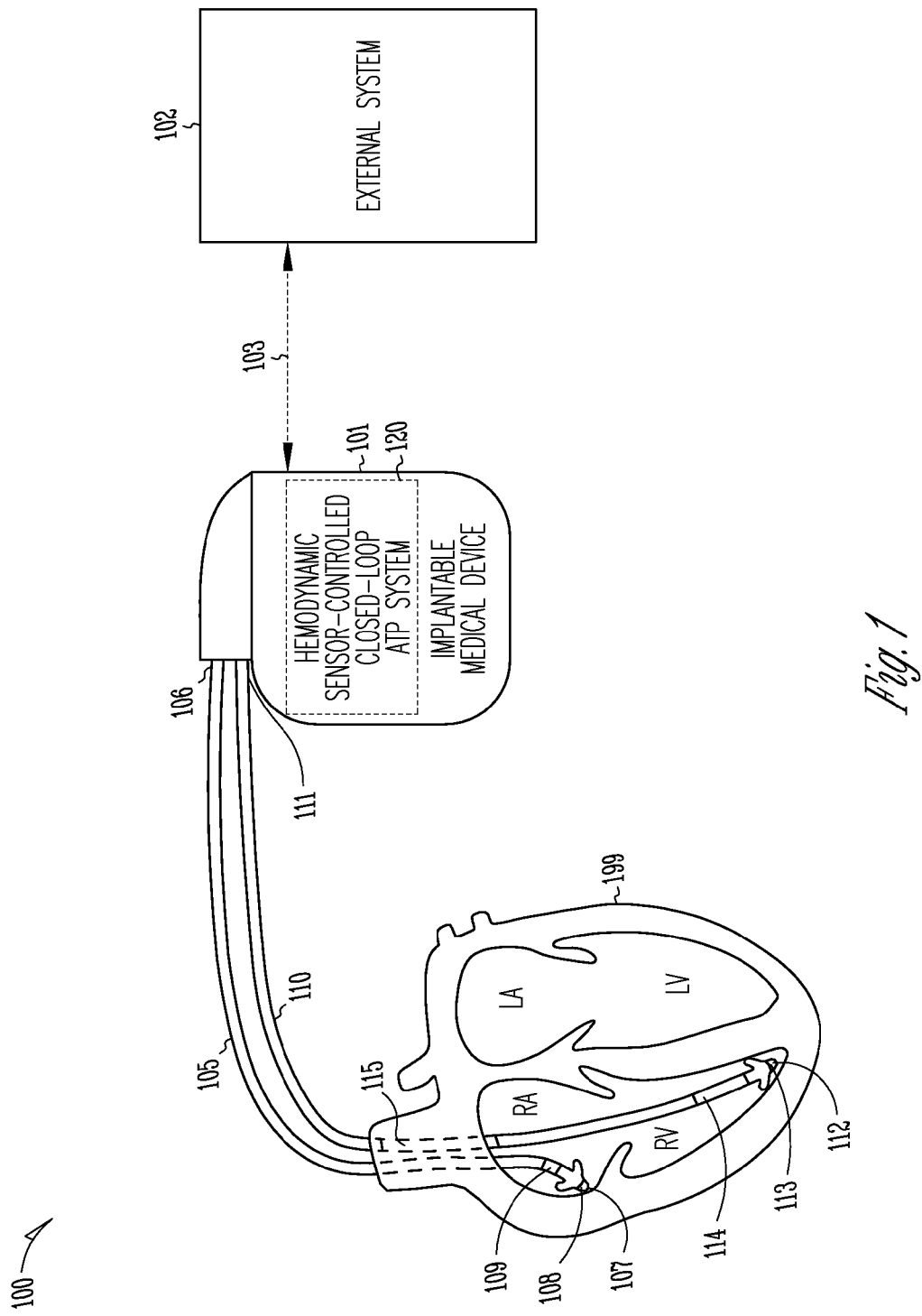
FIG. 1 is an illustration of an embodiment of a CRM system including a hemodynamic sensor-controlled closed-loop ATP system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

This document discusses a CRM system that delivers anti-tachyarrhythmia therapies including ATP. The ATP delivery is controlled by a closed-loop system that automatically verifies whether ATP pulses capture the myocardium and adjusts the ATP delivery based on the outcome of the capture verification. An ATP therapy for VT includes delivery of one or more burst of ATP pulses. In an open-loop system, the response to the delivery of each ATP pulse is not known until a redetection is performed to determine whether the VT sustains after the delivery of a burst of ATP pulses is completed. If the first ATP pulse does not capture the myocardium, one or more remaining ATP pulses of the burst may be delivered during the heart's vulnerable period, thereby posing a risk of accelerating VT to VF. In the present closed-loop system, during a delivery of ATP, the CRM system monitors a hemodynamic signal and determines whether each ATP pulse captures the myocardium by analyzing the effect of the ATP pulse on the hemodynamic signal. When the ATP pulse captures the myocardium, an effective cardiac contraction is indicated by a detectable event in the hemodynamic signal. The effective cardiac contraction is a cardiac contraction that produces a stroke volume that is considered normal or sufficient. It is detected by comparing a hemodynamic parameter derived from the hemodynamic signal to a threshold. The detectable event indicative of the effective cardiac contraction occurs, for example, when the hemodynamic parameter exceeds the threshold. In one embodiment, the hemodynamic signal is a pressure signal indicative of cardiac contractions, and a capture verification is performed by determining whether the ATP pulse results in an effective cardiac contraction. The effective cardiac contraction is detected when a pressure parameter exceeds a threshold. In other words, a cardiac contraction is considered effective when it drives a pressure above a certain level. When an ATP pulse captures the myocardium, the CRM system aborts further delivery of ATP pulses and/or uses the analysis of the hemodynamic signal to optimize ATP parameters for future use. When an ATP pulse fails to capture the myocardium, the CRM system adjusts the current ATP protocol including various ATP parameters. This closed-loop control of ATP delivery provides for optimization of ATP therapy for each individual patient. Because the efficacy of each ATP therapy is known sooner, this closed-loop control of ATP delivery may allow increased number of attempts of terminating VT using ATP therapy without increasing the time allocated for ATP before a defibrillation shock. Because the adjustment of the current ATP protocol potentially enhances the efficacy of ATP, this closed-loop control of ATP delivery may also reduce unnecessary defibrillation shock deliveries.

FIG. 1 is an illustration of an embodiment of a CRM system 100 and portions of the environment in which CRM system 100 operates. CRM system 100 includes an implantable medical device 101 that is electrically coupled to a heart 199 through leads 105 and 110. An external system 102 communicates with implantable medical device 101 via a telemetry link 103.

Implantable medical device 101 delivers anti-tachyarrhythmia therapies including ATP and cardioversion/defibrillation therapies. In one embodiment, implantable medical device 101 is an implantable cardioverter/defibrillator (ICD) with cardiac pacing capabilities. In another embodiment, in addition to a pacemaker and a cardioverter/defibrillator, implantable medical device 101 further includes one or more of other monitoring and/or therapeutic devices such as a neural stimulator, a drug delivery device, and a biological therapy device. Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 as shown in FIG. 1 is typically a pacing lead that includes a proximal end 106 connected to implantable medical device 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow for sensing of the atrial electrogram and/or delivery of atrial pacing pulses. Lead 110 as shown in FIG. 1 is typically a defibrillation lead that includes a proximal end 111 connected to implantable medical device 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows for sensing of the ventricular electrogram and/or delivery of ventricular pacing pulses. Electrodes 114 and 115 allow for sensing of the ventricular electrogram and delivery of ventricular cardioversion/defibrillation pulses.

Implantable medical device 101 includes a hemodynamic sensor-controlled closed-loop ATP system 120. One or more implantable hemodynamic sensors are included in, electrically connected to, and/or wirelessly coupled to implantable medical device 101. System 120 uses at least one hemodynamic signal sensed by an implantable hemodynamic sensor to perform an ATP capture verification. An ATP pulse is considered to have captured the myocardium of heart 199 if an effective cardiac contraction is detected from the hemodynamic signal. The capture verification allows for adjustment and optimization of ATP parameters for individual patients and individual tachyarrhythmia episodes. Various embodiments of system 120 are discussed below. In one embodiment, an implantable pressure sensor senses a blood pressure signal used for the ATP capture verification. The blood pressure signal includes features indicative of cardiac contractions that are detectable by system 120.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system provides for access to implantable medical device 101 from a remote location, such as for monitoring patient status and adjusting therapies. Telemetry link 103 is a wireless communication link providing for bidirectional data transmission between implantable medical device 101 and external system 102. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to enable an available monitoring or therapeutic function (such as ATP), and programming implantable medical device 101 to adjust therapeutic parameters such as pacing and/or cardioversion/defibrillation parameters.

In various embodiments, system 120, including its various specific embodiments discussed below, is implemented by a combination of hardware and software. In various embodiments, system 120 includes elements such as those referred to as modules below that are each an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
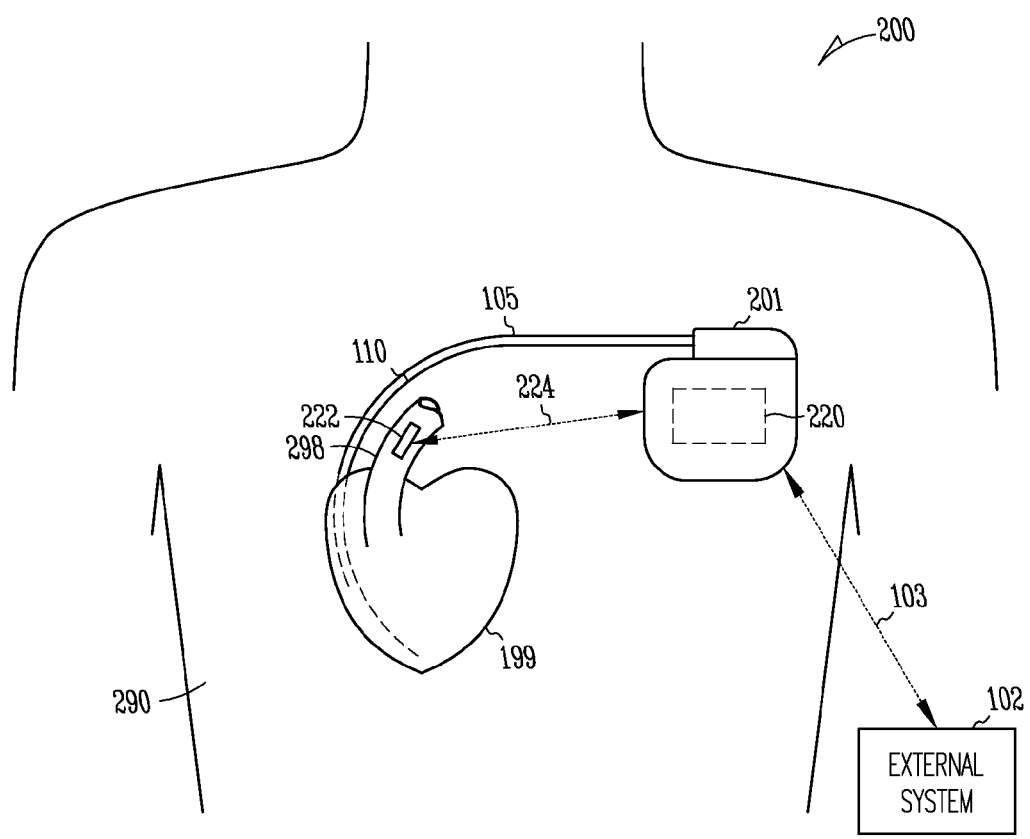
FIG. 2 is an illustration of an embodiment of the CRM system including an implantable pulmonary artery pressure (PAP) sensor.

FIG. 2 is an illustration of an embodiment of a CRM system 200 and portions of an environment in which CRM system 200 operates. CRM system 200 is a specific embodiment of CRM system 100 and includes an implantable pulmonary artery pressure (PAP) sensor 222, an implantable medical device 201, leads 105 and 110, external system 102, a communication link 224 between PAP sensor 222 and implantable medical device 201, and telemetry link 103 between implantable medical device 201 and external system 102.

Implantable medical device 201 is a specific embodiment of implantable medical device 101 and includes a hemodynamic sensor-controlled closed-loop system 220. System 220 is a specific embodiment of system 120 and uses a PAP signal sensed by implantable PAP sensor 222 as the hemodynamic signal to perform the ATP capture verification. The PAP signal is a specific example of the hemodynamic signal used for the ATP capture verification discussed in this document. In general, the hemodynamic signal used for the ATP capture verification includes any blood pressure or other hemodynamic signal from which effective cardiac contractions can be detected by an implantable medical device.

As illustrated in FIG. 2, implantable PAP sensor 222 and implantable medical device 201 are implanted in a body 290 that has a pulmonary artery 298 connected to heart 199. The right ventricle of heart 199 pumps blood through pulmonary artery 298 to the lungs of body 290 to get oxygenated. Implantable PAP sensor 222 is a pressure sensor configured for being affixed to a portion of the interior wall of pulmonary artery 298 to sense a PAP signal. The sensed PAP signal is transmitted to implantable medical device 201 through communication link 224. In one embodiment, communication link 224 includes a wired communication link formed by a lead connected between implantable PAP sensor 222 and implantable medical device 201. In another embodiment, communication link 224 includes an intra-body wireless telemetry link. In a specific embodiment, the intra-body wireless telemetry link is an ultrasonic telemetry link. Implantable medical device 201 includes a sensor signal processing system that receives and processes the PAP signal sensed by implantable PAP sensor 222. In one embodiment, the sensor signal processing system processes the PAP signal by removing unwanted components of the signal that potentially affect the accuracy of the ATP capture verification. In one embodiment, communication link 103 provides for transmission of data representative of the PAP signal sensed by implantable PAP sensor 222 and processed and/or stored in implantable medical device 201. Examples of an implantable PAP sensor and sensor signal processing are discussed in U.S. patent application Ser. No. 11/249,624, entitled "METHOD AND APPARATUS FOR PULMONARY ARTERY PRESSURE SIGNAL ISOLATION," filed on Oct. 13, 2005, now issued as U.S. Pat. No. 7,566,308, assigned to Cardiac Pacemakers, Inc., which is incorporated herein by reference in its entirety.

Figure 3:
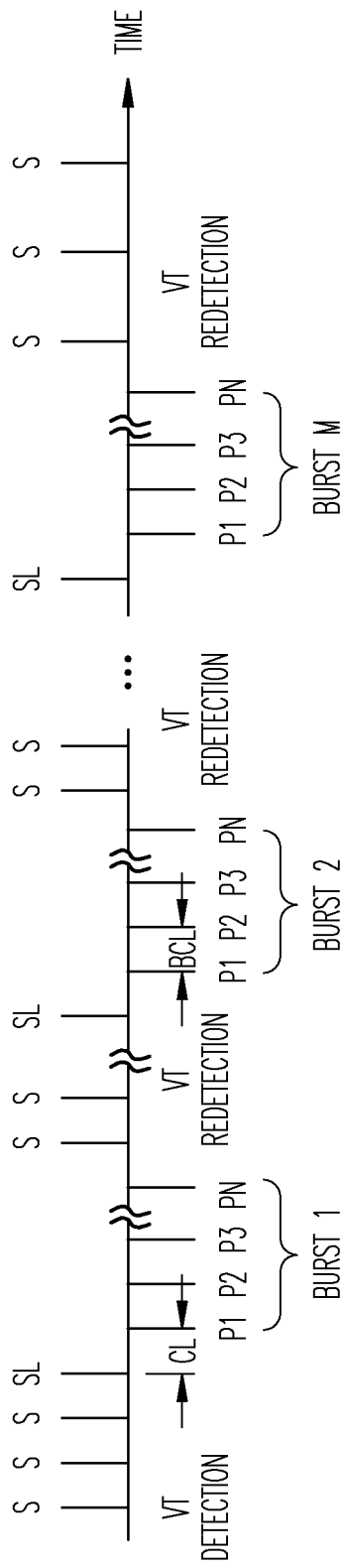
FIG. 3 is a timing diagram illustrating an ATP protocol including ATP parameters.

FIG. 3 is a timing diagram illustrating an ATP protocol including ATP parameters. The illustrated ATP protocol represents a typical protocol in an open-loop ATP system in which no ATP capture verification is performed to adjust the ATP delivery.

In FIG. 3, each S represents a detected intrinsic ventricular depolarization, and SL represents the last intrinsic ventricular depolarization detected before the delivery of a pulse of the ATP pulse is delivered. In response to the detection of a VT episode, an ATP therapy is delivered. The illustrated ATP protocol provides M bursts of ATP pulses (BURST 1, BURST 2, ..., BURST M). Each burst includes N ATP pulses (P1, P2, P3, PN). BURST 1 is delivered after the VT episode is detected. In various embodiments, the VT detection includes an initial detection based on a fast ventricular rate, a verification to confirm that the fast ventricular rate sustains for a certain duration, and a classification to confirm that the fast ventricular rate has a ventricular origin. P1 is delivered when a "coupling interval" expires. The coupling interval (CI) is the time interval between the last detected intrinsic ventricular depolarization (SL) and the first ATP pulse of a burst of ATP pulses (i.e., P1). P2 is delivered when a "burst cycle length" expires. The burst cycle length (BCL) is the pacing interval within the burst of ATP pulses, i.e., the time interval between two successively delivered ATP pulses of the burst of ATP pulses. In other words, CI is the time between P1 and SL, and BCL is the time interval between P(n−1) and P(n), where $2 \leq n \leq N$.

The VT episode is redetected following each burst of ATP pulses is delivered. If the VT episode sustains, the ATP therapy may continue by delivering another burst of ATP pulses. The delivery of the burst of ATP pulses and the VT redetection are repeated until the episode is not redetected or until BURST M has been delivered. If the VT episode is sustains after BURST M has been delivered, one or more defibrillation shocks are delivered to terminate the VT episode.

During the ATP therapy, the BCL may be a constant or varying time interval. A "burst" scheme of BCL refers to a BCL that is a constant time interval throughout the ATP therapy. A "ramp" scheme of BCL refers to a BCL that is decremental within each burst of ATP pulses. A "scan" scheme of BCL refers to a BCL that is decremental from a burst of ATP pulses to the next burst of ATP pulses within an ATP therapy. In various embodiment, an ATP protocol includes a plurality of ATP parameters including CI, BCL, BCL scheme (burst, ramp, or scan), number of pulses per burst (N), and number of burst per ATP therapy (per ATP protocol)(M).

In a typical open-loop ATP system, the effect of the ATP pulses is not known until the VT redetection period that follows. Consequently, some of the ATP pulses may be unnecessary, ineffective, or even risky. As discussed in detail below, a hemodynamic signal-based ATP capture verification during the delivery of each burst of ATP pulses eliminates the delivery of such unnecessary, ineffective, or risky ATP pulses.

Figure 4:
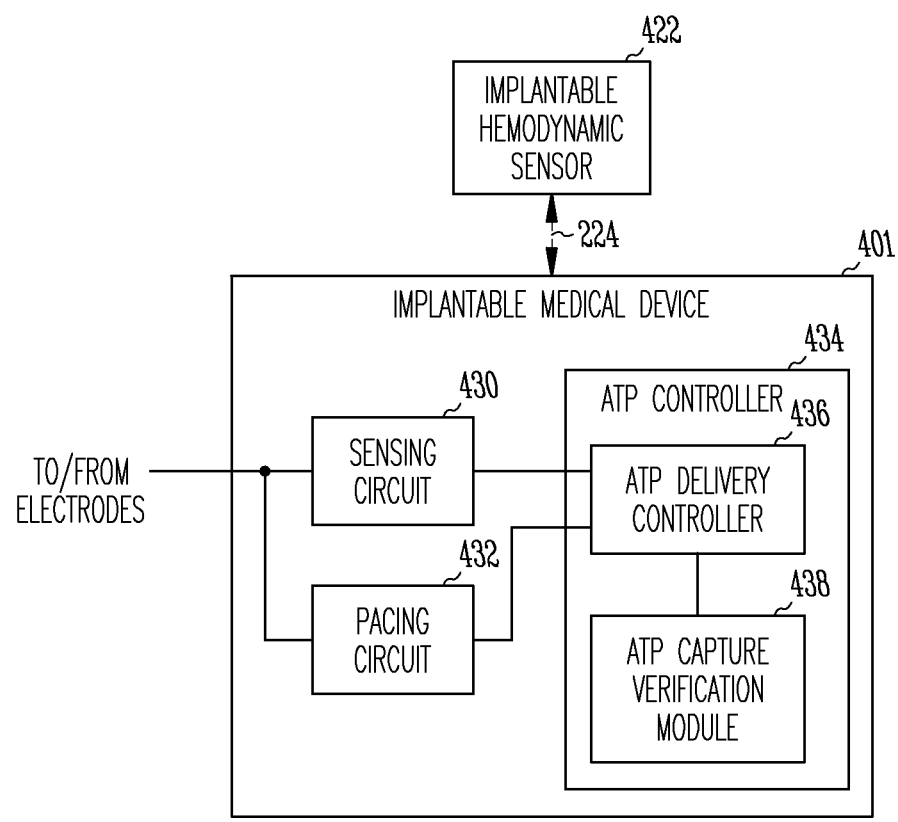
FIG. 4 is a block diagram illustrating an embodiment of portions of the hemodynamic sensor-controlled closed-loop ATP system.

FIG. 4 is a block diagram illustrating an embodiment of portions of system 100, including an implantable hemodynamic sensor 422, an implantable medical device 401, and communication link 224. Implantable hemodynamic sensor 422 senses a hemodynamic signal indicative of cardiac contractions. Implantable medical device 401 is a specific embodiment of implantable medical device 101 and includes a sensing circuit 430, a pacing circuit 432, and an ATP controller 434. Sensing circuit 430 senses one or more cardiac signals. Pacing circuit 432 delivers pacing pulses including ATP pulses. ATP controller 434 includes an ATP delivery controller 436 and an ATP capture verification module 438. ATP delivery controller 436 controls the delivery of the ATP pulses according to an ATP protocol. ATP capture verification module 438 performs an ATP capture verification during the delivery of the ATP pulses by detecting an effective cardiac contraction using the hemodynamic signal sensed by implantable hemodynamic sensor 422.

Figure 5:
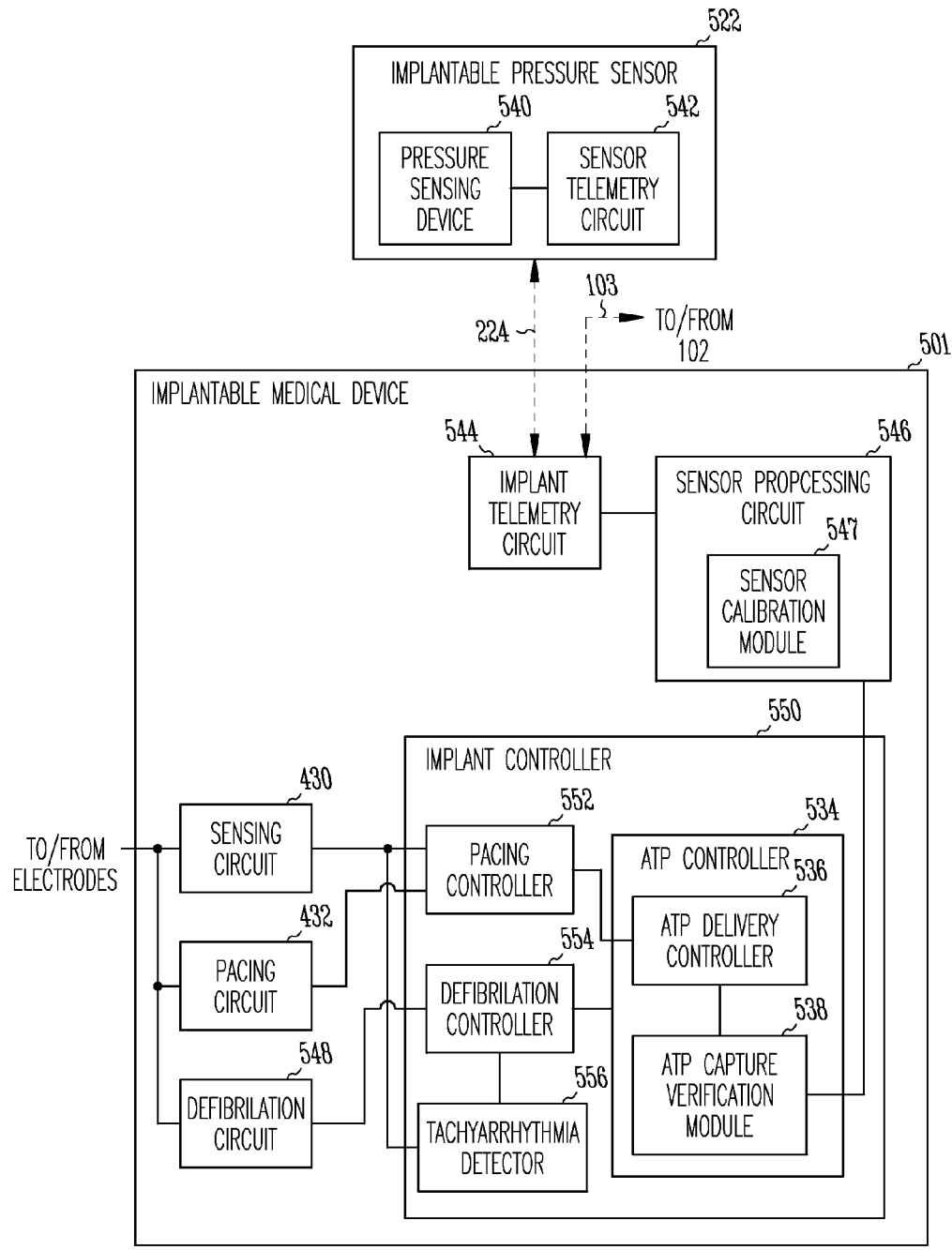
FIG. 5 is a block diagram illustrating a specific embodiment of portions of the hemodynamic sensor-controlled closed-loop ATP system.

FIG. 5 is a block diagram illustrating a specific embodiment of portions of system 100, including an implantable pressure sensor 522, an implantable medical device 501, and communication link 224.

Implantable pressure sensor 522 is a specific embodiment of implantable hemodynamic sensor 422 and senses a blood pressure signal indicative of cardiac contractions. In one embodiment, implantable pressure sensor 522 is an implantable PAP sensor configured to be placed in the pulmonary artery and communicatively coupled to implantable medical device 501 via communication link 224, such as implantable PAP sensor 222. In one embodiment, implantable pressure sensor 522 includes a pressure sensing device 540 and a sensor telemetry circuit 542. Pressure sensing device 540 is a transducer that converts a pressure to an electrical signal. Sensor telemetry circuit 542 transmits data representative of the PAP signal to implantable medical device 501 via communication link 224, which is a telemetry link such as an ultrasonic telemetry link. In other embodiments, implantable pressure sensor 522 is included in implantable medical device 501 or electrically connected to implantable medical device 501 via a lead.

Implantable medical device 501 is a specific embodiment of implantable medical device 401 and includes implant telemetry circuit 544, sensor processing circuit 546, sensing circuit 430, pacing circuit 432, defibrillation circuit 548, and implant controller 550. Implant telemetry circuit 544 receives the blood pressure signal sensed by implantable pressure sensor 522 and transmitted via communication link 224. In addition, implant telemetry circuit 544 transmits data to, and receives data from, external system 102 via telemetry link 103. In one embodiment, communication link 224 is an acoustic telemetry link, and telemetry link 103 is an RF telemetry link. Implant telemetry circuit 544 includes an implant acoustic telemetry circuit to transmit and receive signals via the acoustic telemetry link and an implant RF telemetry circuit to transmit and receive signals via the RF telemetry link. Sensor processing circuit 546 processes the blood pressure signal to allow or facilitate the detection of effective cardiac contractions. In one embodiment, sensor processing circuit 546 includes a sensor calibration module 547 that removes environmental effects from the blood pressure signal. In various embodiments, sensor processing circuit 546 removes components of the blood pressure signal that affect accuracy of the detection of effective cardiac contractions. For example, effects of respiration on the blood pressure signal is removed by filtering, and effects of posture on the blood pressure signal is removed by using a posture signal sensed by a posture sensor. In one embodiment, the blood pressure signal is a PAP signal. Examples of processing a PAP signal is discussed in U.S. patent application Ser. No. 11/249,624.

Sensing circuit 430 senses one or more cardiac signals. Pacing circuit 432 deliver pacing pulses including ATP pulses. Defibrillation circuit 548 delivers cardioversion/defibrillation shocks. Implant controller 550 includes a pacing controller 552, defibrillation controller 554, tachyarrhythmia detector 556, and ATP controller 534. Pacing controller 552 controls the delivery of the pacing pulses. In one embodiment, as illustrated in FIG. 5, ATP controller 534 controls the delivery of the ATP pulses through pacing controller 552. For example, ATP controller 534 executes the ATP protocol to generate ATP pulse delivery signals, and pacing controller 552 directly controls the delivery of the pacing pulses from pacing circuit 432 using the delivery timing signals. Defibrillation controller 554 controls the delivery of cardioversion/defibrillation shocks. Tachyarrhythmia detector 556 detects tachyarrhythmia episodes and identifies predetermined type tachyarrhythmia episodes that are likely terminable by ATP. In one embodiment, the predetermined type tachyarrhythmia episodes include VT episodes, and tachyarrhythmia detector 556 includes a VT detector to detect VT episodes. The VT detector performs the VT detection and redetections illustrated in FIG. 3. In one embodiment, the VT detector detects and confirms VT before ATP controller 534 is activated to control the delivery of an ATP therapy. In one embodiment, the VT detector also extracts parameters indicative of characteristics of the VT episode from at least the one or more cardiac signals, such as heart rate and heart rate stability parameters.

ATP controller 534 is a specific embodiment of ATP controller 434 and includes an ATP delivery controller 536 and an ATP capture verification module 538. ATP delivery controller 536 controls the delivery of the ATP pulses according to the ATP protocol. ATP capture verification module 538 performs an ATP capture verification during the delivery of the ATP pulses by detecting an effective cardiac contraction using the blood pressure signal.

Figure 6:
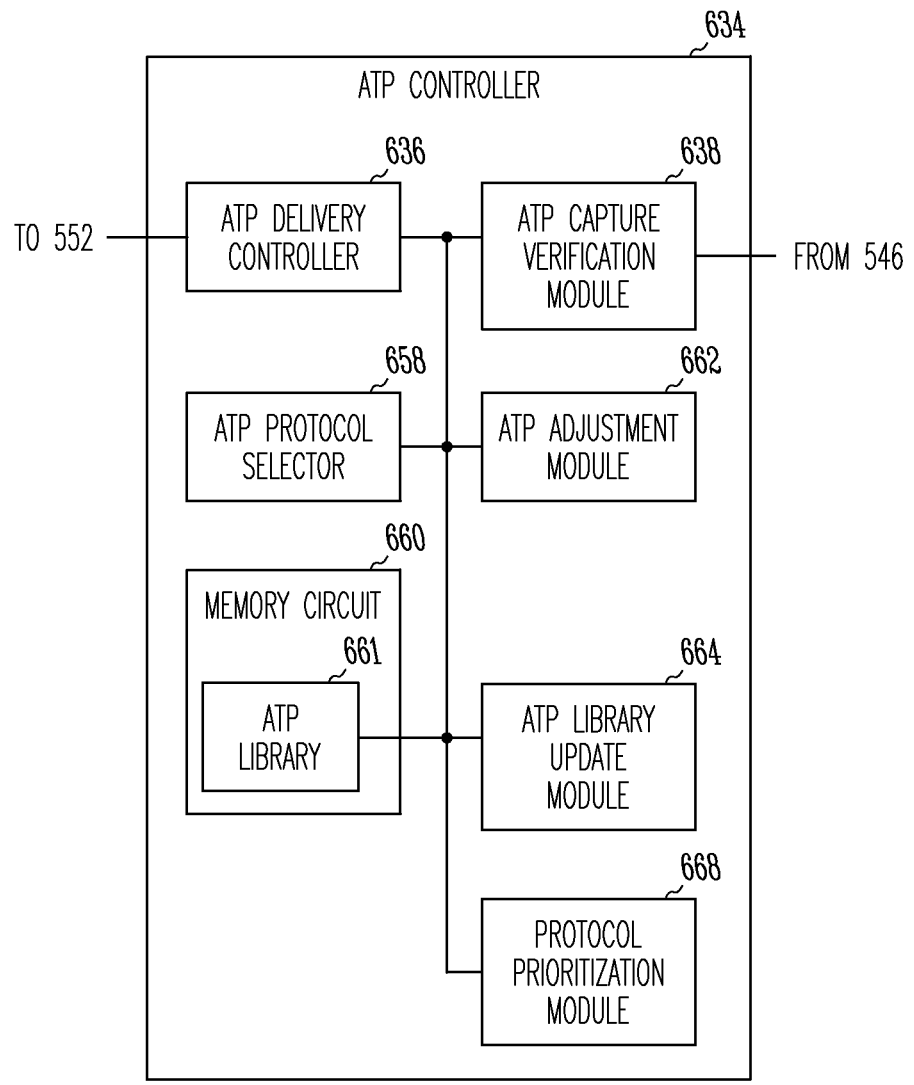
FIG. 6 is a block diagram illustrating an embodiment of an ATP controller of the hemodynamic sensor-controlled closed-loop ATP system.

FIG. 6 is a block diagram illustrating an embodiment of an ATP controller 634, which is a specific embodiment of ATP controller 434 or 534. ATP controller 634 controls an ATP therapy in response to the detection of the predetermined type tachyarrhythmia episode such as the VT episode. ATP controller 634 includes an ATP delivery controller 636, an ATP capture verification module 638, an ATP protocol selector 658, an ATP adjustment module 662, a memory circuit 660, an ATP library update module 664, and a protocol prioritization module 668.

ATP delivery controller 636 is a specific embodiment of ATP delivery controller 436 or 536 and controls the delivery of the ATP pulses according to a selected ATP protocol. In one embodiment, ATP delivery controller 636 is activated when a VT episode is detected and confirmed. ATP delivery controller 636 is reset to switch from the selected ATP protocol to a new ATP protocol in response to a reset signal produced as an outcome of the ATP capture verification. That is, in response to the reset signal, ATP delivery controller 636 stops controlling the delivery of the ATP pulses according to the selected ATP protocol and starts to control the delivery of the ATP pulses according to a new ATP protocol. ATP capture verification module 638 is a specific embodiment of ATP capture verification module 438 or 538 and performs the ATP capture verification by extracting a hemodynamic parameter from the hemodynamic signal and comparing the hemodynamic parameter to a capture threshold to detect effective cardiac contractions. ATP capture verification module 638 is further discussed below with reference to FIG. 7.

ATP protocol selector 658 selects the ATP protocol from a plurality of stored ATP protocols. In one embodiment, ATP protocol selector 658 selects the ATP protocol based on the parameters indicative of characteristics of the tachyarrhythmia episode, such as heart rate and heart rate stability parameters produced by tachyarrhythmia detector 556. In another embodiment, ATP protocol selector 658 selects the ATP protocol based on a priority code assigned to each of the stored ATP protocols.

ATP adjustment module 662 adjusts the ATP protocol based on an outcome of the ATP capture verification. If an ATP capture is verified (an effective cardiac contraction is detected by ATP capture verification module 638), in one embodiment, the delivery of the ATP pulses according to the selected ATP protocol is aborted, and the tachyarrhythmia episode is redetected to determine whether it has been terminated. In another embodiment, the delivery of the ATP pulses according to the selected ATP protocol is completed to evaluate the selected ATP protocol for ATP parameter optimization purposes. In one embodiment, ATP adjustment module 662 produces a new ATP protocol by using values of the ATP parameters associated with the a verified ATP capture. If no ATP capture is verified (i.e., a loss of capture is verified), in one embodiment, ATP adjustment module 662 aborts the delivery of the ATP pulses, produces a new ATP protocol, and produces the reset signal to reset ATP delivery controller 636. In one embodiment, ATP adjustment module 662 produces the new ATP protocol by adjusting the ATP parameters of the selected protocol, such as by increasing CI, increasing BCL, and/or changing BCL scheme. In another embodiment, ATP adjustment module 662 produces the new ATP protocol by selecting another ATP protocol from the plurality of store ATP protocols. In one embodiment, ATP adjustment module 662 repeats producing the reset signal and the new ATP protocol if no ATP capture is verified for up to a predetermined number of times (such as 4 times). If the delivery of the ATP pulses is aborted because the ATP capture is not verified, there is no need to determine whether hemodynamic episode has been terminated by ATP.

Memory circuit 660 is a data storage device that includes an ATP library 661. ATP library 661 includes the plurality of stored ATP protocols. ATP library update module 664 updates ATP library 661 after each delivery of the ATP therapy. In one embodiment, ATP library update module 664 updates a success rate associated with each of the stored ATP protocols. The success rate is statistically produced and updated to indicate a likeliness of terminating a tachyarrhythmia episode using the associated ATP protocol. In one embodiment, the parameters indicative of characteristics of a particular tachyarrhythmia episode, such as heart rate and heart rate stability parameters, are also stored in association with a stored ATP protocol that has been used to successfully terminate that particular tachyarrhythmia episode. In one embodiment, if an ATP protocol is adjusted by ATP adjustment module 662 during an ATP therapy, and the adjusted protocol is used to successfully terminate a tachyarrhythmia episode, the adjusted (new) ATP protocol is added to the plurality of stored ATP protocols in ATP library 661.

Protocol prioritization module 668 assigns the priority code to each of the stored ATP protocols based on the success rate associated with that stored ATP protocol. In one embodiment, protocol prioritization module 668 also assigns the priority code based on the parameters of the stored ATP protocol. For example, a higher priority is given to an ATP protocol that has relatively fewer ATP pulses per burst or otherwise requires less time to deliver the ATP pulses.

Figure 7:
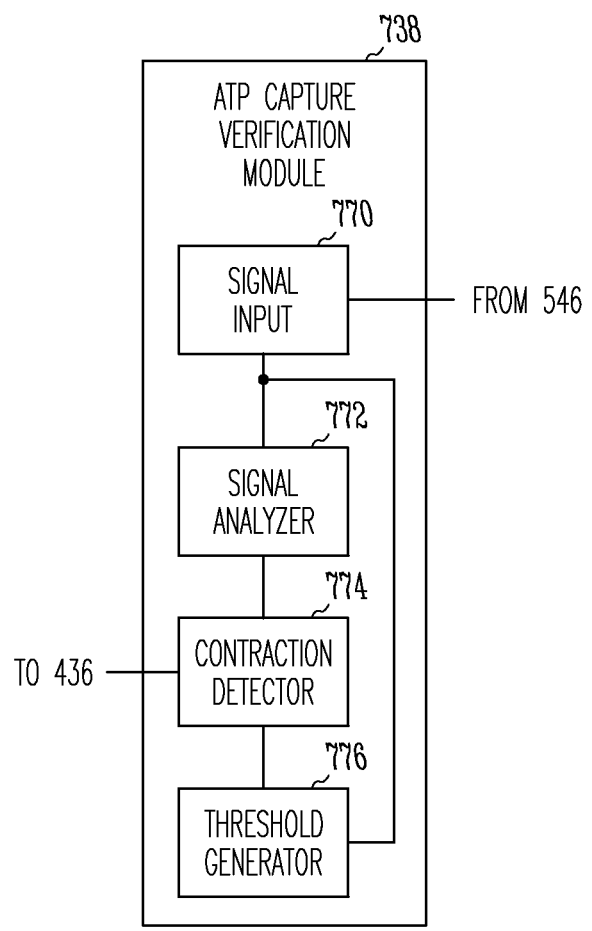
FIG. 7 is a block diagram illustrating an embodiment of an ATP verification module of the ATP controller.

FIG. 7 is a block diagram illustrating an embodiment of an ATP capture verification module 738. ATP verification module 738 is a special embodiment of ATP verification module 638 and includes a signal input 770, a signal analyzer 772, a contraction detector 774, and a threshold generator 776.

Signal input 770 receives the hemodynamic signal. Signal analyzer 772 extracts the hemodynamic parameter from the hemodynamic signal. Contraction detector 774 detects the effective cardiac contraction by comparing the hemodynamic parameter to the capture threshold. Threshold generator 776 produces the capture threshold. In one embodiment, threshold generator 776 produces the capture threshold based on a baseline value of the hemodynamic parameter extracted from the hemodynamic signal sensed during a normal sinus rhythm. The capture threshold is set to a predetermined percentage of the baseline value of the hemodynamic parameter.

In one embodiment, in which the hemodynamic signal is a blood pressure signal such as a PAP signal, ATP capture verification module 738 performs the ATP capture verification by detecting effective cardiac contractions from the blood pressure signal during the ATP therapy. Signal input 770 receives the blood pressure signal. Signal analyzer 772 extracts a pressure parameter from the pressure signal. In one embodiment, the pressure parameter is a pulse pressure being a difference between a systolic pressure and a diastolic pressure. Using the pulse pressure for ATP capture verification has an advantage of being able to ignore many unwanted components because they are canceled out when the difference is calculated. When desired, this allows suspension of the hemodynamic signal calibration during the ATP therapy. In another embodiment, the pressure parameter is mean pressure being the amplitude of the blood pressure signal averaged over a predetermined time interval or a predetermined number of heart beats. The mean pressure represents the DC or low-frequency component of the blood pressure signal. In another embodiment, the pressure parameter is a peak pressure being a peak amplitude of the blood pressure signal. In another embodiment, the pressure parameter is a pressure power being a power in a predetermined frequency band. Contraction detector 774 detects evoked pressure responses each indicative of an effective cardiac contraction by comparing the pressure parameter to a capture threshold pressure. Threshold generator 776 produces the capture threshold pressure. In one embodiment, threshold generator 776 produces the capture threshold pressure based on a baseline value of the pressure parameter extracted from the blood pressure signal sensed during a normal sinus rhythm. The capture threshold pressure is set to a predetermined percentage of the baseline value of the pressure parameter.

Figure 8:
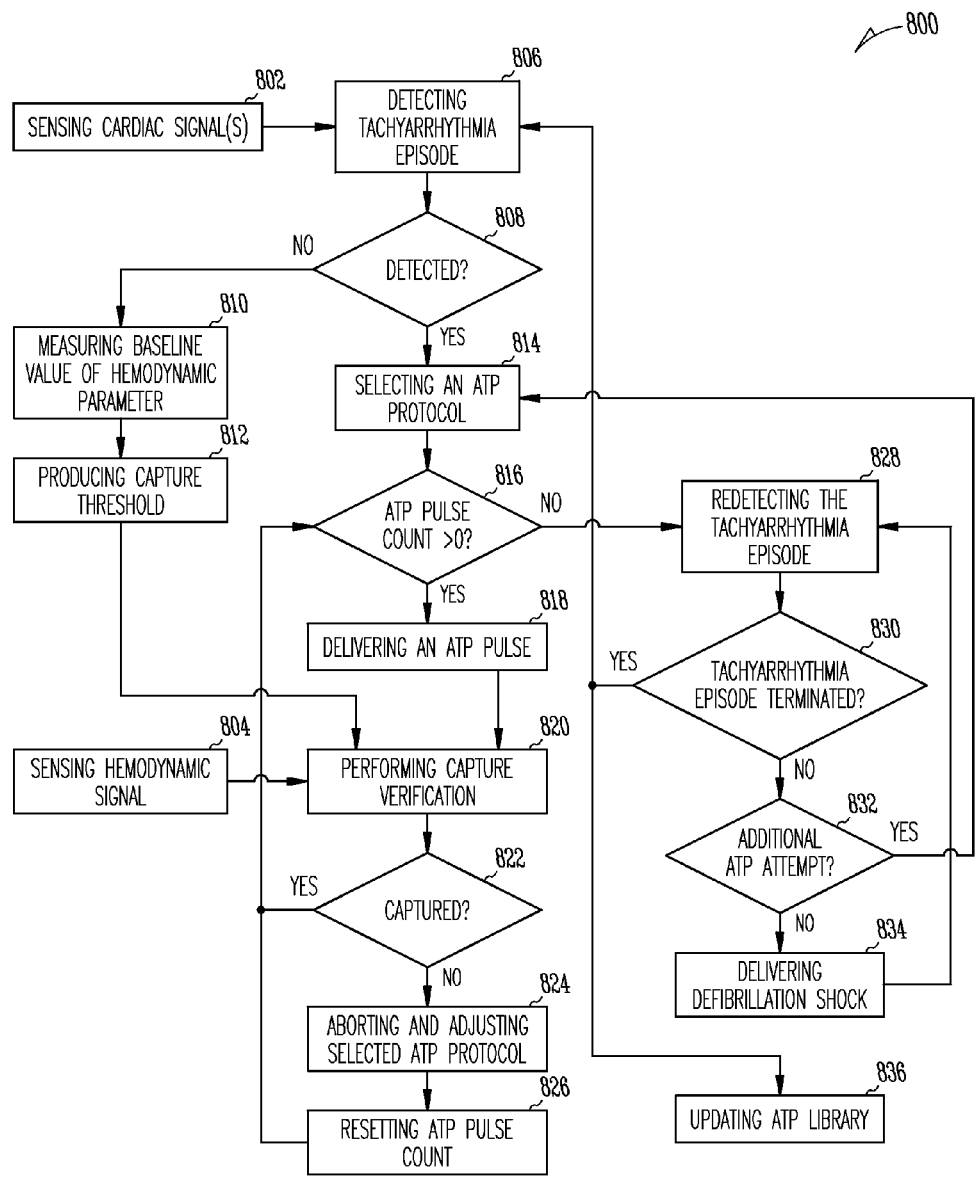
FIG. 8 is a flow chart illustrating an embodiment of a method for controlling ATP using a hemodynamic signal.

FIG. 8 is a flow chart illustrating an embodiment of a method 800 for controlling ATP using a hemodynamic signal. In one embodiment, method 800 is performed by system 100, including its various embodiments discussed in this document.

One or more cardiac signals are sensed at 802. A hemodynamic signal is sensed at 804. In one embodiment, the hemodynamic signal is a blood pressure signal. In one embodiment, the hemodynamic signal is processed to remove unwanted components such as effects of respiration and effects of posture. In a specific embodiment, the blood pressure signal is a PAP signal sensed using an implantable PAP sensor configured to be placed in the pulmonary artery. Examples of sensing and processing a PAP signal are discussed in U.S. patent application Ser. No. 11/249,624, now issued as U.S. Pat. No. 7,566,308.

A predetermined type tachyarrhythmia episode is being detected at 806. This predetermined type is known to be likely terminable by ATP, such as monomorphic VT. In one embodiment, a VT episode is detected when a fast ventricular rate is detected, verified to be sustaining, and confirmed to be of a ventricular origin. In one embodiment, parameters indicative of characteristics of the detected tachyarrhythmia episode, such as the heart rate and heart rate stability, are extracted from at least the one or more cardiac signals for storage in association with a stored ATP protocol that has been used to successfully terminate that tachyarrhythmia episode.

If the predetermined type tachyarrhythmia episode is not detected at 808, a baseline value of a hemodynamic parameter may be measured at 810. In one embodiment, the hemodynamic signal is a blood pressure signal, and the hemodynamic parameter is a pressure parameter. A capture threshold is produced at 812 using the measured baseline value. In one embodiment, the capture threshold is set to a predetermined percentage of the baseline value. In one embodiment, the capture threshold is updated substantially continuously to follow the change in the baseline pressure in a patient. In another embodiment, the capture threshold is updated on a periodic basis. In another embodiment, the capture threshold is updated upon a user request.

If the predetermined type tachyarrhythmia episode is detected at 808, an ATP protocol is selected from a plurality of stored ATP protocols at 814. In one embodiment, the ATP protocol is selected based on the parameters indicative of characteristics of the detected tachyarrhythmia episode. In one embodiment, the ATP protocol is selected based on a priority code assigned to each of the stored ATP protocols. The priority code is produced based on the historical performance of each stored ATP protocol and the parameters of that ATP protocol.

A burst of ATP pulses is to be delivered with the number of ATP pulses specified in the selected ATP protocol. If an ATP pulse count is greater than zero (i.e., there are remaining ATP pulse(s) to be delivered) at 816, an ATP pulse is delivered at 818. A capture verification is performed at 820. The ATP capture verification includes determining whether the ATP pulse delivered at 818 causes an effective cardiac contraction. The hemodynamic parameter is extracted from the hemodynamic signal sensed during the ATP therapy. The effective cardiac contraction is detected by comparing the hemodynamic parameter to the capture threshold. In one embodiment, the hemodynamic signal is a blood pressure signal. A pressure parameter is extracted from the pressure signal sensed during the ATP therapy. Examples of the pressure parameter includes a pulse pressure being a difference between a systolic pressure and a diastolic pressure, a mean pressure being an average amplitude (DC or low-frequency value) of the pressure signal, a peak pressure, and a pressure power being a power in a predetermined frequency band. An evoked pressure response indicative of an effective cardiac contraction is detected by comparing the pressure parameter to a capture threshold pressure.

If the myocardium is captured at 822, and the ATP pulse count is greater than zero at 816, another ATP pulse is delivered at 818. If the myocardium is captured at 822, and the ATP pulse count reaches zero at 816, the tachyarrhythmia episode is redetected at 828. In one embodiment, if the myocardium is captured at 822, the ATP pulse count is set to zero, thereby aborting further delivery of the ATP pulses. In another embodiment, if the myocardium is captured at 822, the ATP pulses are continued to be delivered according to the selected ATP protocol for the purpose of evaluating the parameters of the selected ATP protocol for protocol optimization.

If the myocardium is not captured at 822, the selected ATP protocol is aborted and adjusted to produce a new ATP protocol at 824. In one embodiment, the new ATP protocol is produced by adjusting ATP parameters, such as by increasing CI, increasing BCL, and/or changing the BCL scheme from burst to ramp. In another embodiment, the new ATP protocol is produced by selecting another ATP protocol from the plurality of store ATP protocols.

The ATP pulse count is reset at 826. The delivery of the ATP pulses is restarted according to the new ATP protocol. Steps 816, 818, 820, 822, 824, and 826 are repeated until the ATP pulse count equals zero at 816. The ATP pulse count reaches zero at 816 when the ATP capture is verified, when a complete burst of ATP pulses is delivered, or when the ATP pulse count is otherwise set to zero as programmed.

If the ATP pulse count equals zero at 816, the tachyarrhythmia episode is redetected at 828 to determine whether the tachyarrhythmia episode sustains. If the tachyarrhythmia episode has been terminated at 830, the ATP library is updated at 836. In one embodiment, a success rate associated with each stored ATP protocol is updated each time when that stored ATP protocol is used to reflect the efficacy of ATP therapy associated with that stored ATP protocol. In one embodiment, the parameters indicative of the characteristics of the tachyarrhythmia episode associated with that stored ATP protocol are also stored to allow future ATP protocol selection using parameter matching as a factor. In one embodiment, the new ATP protocol produced during the ATP therapy by adjusting the selected ATP protocol is added to the plurality of stored ATP protocols if the tachyarrhythmia episode is terminated in response to the delivery of the ATP pulses according to the new ATP protocol. In one embodiment, the priority code of each of the stored ATP protocols is updated after each ATP therapy to reflect the result of that ATP therapy in association with the stored ATP protocols.

If the tachyarrhythmia episode is not terminated at 830, and no additional ATP attempt is to be made at 832, a defibrillation shock is delivered at 834. Steps 828, 830, 832, and 834 are repeated until the tachyarrhythmia episode is terminated at 830 or until a certain number of defibrillation shocks have been delivered. Generally, if a defibrillation shock has been delivered at 834, no additional ATP attempt is to be made at 832.

If the tachyarrhythmia episode is not terminated at 830, and an additional ATP attempt is to be made at 832, method 800 is repeated from selecting another ATP protocol at 814. In one embodiment, additional ATP attempts are made until a predetermined maximum number of ATP attempts have been made. If the tachyarrhythmia is terminated at 830 following the delivery of the defibrillation shock at 834, the success rate associated with each stored ATP protocol used in the ATP attempt(s) is updated to reflect the unsuccessful attempt(s) associated with that stored ATP protocol.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for anti-tachyarrhythmia pacing (ATP), the method comprising:
    sensing a hemodynamic signal;
    detecting a predetermined type tachyarrhythmia episode;
    delivering ATP pulses according to an ATP protocol in response to the detection of the predetermined type tachyarrhythmia episode; and
    performing an ATP capture verification during the delivery of the ATP pulses by detecting an effective cardiac contraction using the hemodynamic signal, the effective cardiac contraction indicated by a detectable event in the hemodynamic signal.

2. The method of claim 1, wherein performing the ATP capture verification comprises:
    extracting a hemodynamic parameter from the hemodynamic signal; and
    detecting the effective cardiac contraction by comparing the hemodynamic parameter to a capture threshold.

3. The method of claim 2, wherein sensing the hemodynamic signal comprises sensing a blood pressure signal, and performing the ATP capture verification comprises:
    extracting a pressure parameter from the pressure signal; and
    detecting an evoked pressure response indicative of the effective cardiac contraction by comparing the pressure parameter to a capture threshold pressure.

4. The method of claim 3, wherein extracting the pressure parameter comprises extracting a pulse pressure being a difference between a systolic pressure and a diastolic pressure.

5. The method of claim 3, wherein extracting the pressure parameter comprises extracting a mean pressure being an amplitude of the blood pressure signal averaged over a predetermined duration or a predetermine number of heart beats.

6. The method of claim 3, wherein sensing the blood pressure signal comprises sensing an pulmonary artery pressure (PAP) signal using an implantable PAP sensor.

7. The method of claim 1, further comprising adjusting the ATP protocol based on an outcome of the ATP capture verification.

8. The method of claim 7, further comprising aborting the delivery of the ATP pulses if the effective cardiac contraction is detected.

9. The method of claim 7, further comprising aborting the delivery of the ATP pulses and delivering additional ATP pacing pulses according to a new ATP protocol if the effective cardiac contraction is not detected.

10. The method of claim 9, further comprising producing the new ATP protocol by adjusting ATP parameters of the ATP protocol.

11. The method of claim 9, further comprising producing the new ATP protocol by selecting another ATP protocol from a plurality of stored ATP protocols.

12. The method of claim 11, further comprising:
    maintaining an ATP library including a plurality of stored ATP protocols each including a plurality of ATP parameters; and
    selecting the ATP protocol from the plurality of stored ATP protocols based on priority codes each associated with one ATP protocol of the plurality of stored ATP protocols.

13. The method of claim 12, wherein maintaining the ATP library comprises:
    updating a success rate associated with the ATP protocol based on an outcome of the capture verification; and adjusting the priority codes based on the success rates associated with the stored ATP protocols and the ATP parameters of the stored ATP protocols.

14. The method of claim 12, further comprising:
sensing one or more cardiac signals;
detecting the predetermined type tachyarrhythmia episode using the one or more cardiac signals; and
extracting parameters indicative of characteristics of the detected predetermined type tachyarrhythmia episode from at least the one or more cardiac signals,
and wherein selecting the ATP protocol comprises selecting the ATP protocol from the plurality of stored ATP protocols based on the parameters indicative of characteristics of the detected predetermined type tachyarrhythmia episode and the priority codes.

15. A method for anti-tachyarrhythmia pacing (ATP), the method comprising:
receiving a pulmonary artery pressure (PAP) signal;
detecting a tachyarrhythmia episode;
delivering ATP pulses from an implantable medical device according to an ATP protocol in response to the detection of the tachyarrhythmia episode; and
performing an ATP capture verification during the delivery of the ATP pulses by detecting an effective cardiac contraction using the PAP signal.

16. The method of claim 15, wherein receiving the PAP signal comprises receiving the PAP signal from an implantable PAP sensor placed in a pulmonary artery and communicatively coupled to the implantable medical device.

17. The method of claim 16, wherein receiving the PAP signal from the implantable PAP sensor comprises receiving the PAP signal from the implantable PAP sensor via a wireless telemetry link.

18. The method of claim 17, wherein receiving the PAP signal from the implantable PAP sensor comprises receiving the PAP signal from the implantable PAP sensor via an ultrasonic telemetry link.

19. The method of claim 15, comprising:
sensing one or more cardiac signals;
detecting a ventricular tachyarrhythmia (VT) episode;
extracting parameters indicative of characteristics of the detected VT episode from at least the one or more cardiac signals; and
selecting the ATP protocol from an ATP library based on the parameters indicative of the characteristics of the detected VT episode, the ATP library including a plurality of stored ATP protocols.

20. The method of claim 19, wherein selecting the ATP protocol comprises selecting the ATP protocol based on a priority code assigned to each of the stored ATP protocols, and further comprising updating the ATP library, including updating the priority codes, using an outcome of the ATP capture verification.

* * * * *